(12) United States Patent
Chang

(10) Patent No.: US 11,804,147 B2
(45) Date of Patent: Oct. 31, 2023

(54) PERSONALIZED WEIGHT MANAGEMENT

(71) Applicant: LG ELECTRONICS INC., Seoul (KR)

(72) Inventor: Seo Jeong Chang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 674 days.

(21) Appl. No.: 16/730,647

(22) Filed: Dec. 30, 2019

(65) Prior Publication Data

US 2021/0118328 A1 Apr. 22, 2021

(30) Foreign Application Priority Data

Oct. 18, 2019 (KR) .................. 10-2019-0130013

(51) Int. Cl.
*G09B 19/00* (2006.01)
*A61B 5/00* (2006.01)
*G16H 20/60* (2018.01)
*A63B 24/00* (2006.01)
*G16H 20/30* (2018.01)

(52) U.S. Cl.
CPC .......... *G09B 19/0092* (2013.01); *A61B 5/486* (2013.01); *A61B 5/4866* (2013.01); *A61B 5/7267* (2013.01); *A61B 5/7275* (2013.01); *A63B 24/0062* (2013.01); *G16H 20/30* (2018.01); *G16H 20/60* (2018.01)

(58) Field of Classification Search
CPC ................................................ G09B 19/0092
USPC ........................................................ 434/127
See application file for complete search history.

(56) References Cited

U.S. PATENT DOCUMENTS

2011/0143322 A1  6/2011  Tsang
2016/0166195 A1* 6/2016  Radecka ............... A61B 5/112
                                              600/595

FOREIGN PATENT DOCUMENTS

KR       10-1740516 B1     6/2017
KR       10-1987620 B1     6/2019

* cited by examiner

*Primary Examiner* — Kesha Frisby
(74) *Attorney, Agent, or Firm* — Birch, Stewart, Kolasch & Birch, LLP

(57) ABSTRACT

The present disclosure relates to an apparatus for managing an individual's weight, which operates in an Internet of Things environment over a 5G communication network and is capable of effectively managing an individual's weight, and a personalized weight management method using the apparatus. The present disclosure is directed to learning a predicted weight of an individual calculated based on weight information of the individual, information on a type and an amount of food ingested by the individual, and information on exercise performed by the individual, received on the present day, and predicting information on food to be ingested and information on exercise to be performed in order to achieve a target weight received from the individual, based on the learned predicted weight.

20 Claims, 8 Drawing Sheets

PERSONALIZED WEIGHT MANAGEMENT

CROSS-REFERENCE TO RELATED APPLICATION

This present application claims benefit of priority to Korean Patent Application No. 10-2019-0130013 entitled "PERSONALIZED WEIGHT MANAGEMENT," filed on Oct. 18, 2019, in the Republic of Korea, the entire disclosure of which is incorporated herein by reference.

BACKGROUND

1. Technical Field

The present disclosure relates to an apparatus for effectively managing an individual's weight and a personalized weight management method using the same.

2. Description of Related Art

The following description is only for the purpose of providing background information related to embodiments of the present disclosure, and the contents to be described do not necessarily constitute related art.

Obesity refers to excessive accumulation of body fat in the body, which is caused by prolonged periods of energy imbalance in which the energy ingested exceeds the energy consumed. The prevalence of obesity has increased significantly in the recent 30 years due to increased animal food intake, lack of physical activity, and stress. Obesity, which refers to excessive accumulation of fatty tissue in the body, is becoming a global problem, to the extent that the World Health Organization warns that obesity is a disease requiring a long-term struggle.

Moreover, obesity is not just an aesthetic problem, but a direct cause of metabolic syndrome, and can result in various diseases such as cancer, heart disease, diabetes, high blood pressure, stroke, and osteoarthritis. In fact, obese people are reported to have a 28% higher mortality rate, a 2.9 times higher risk of diabetes, and a 5.6 times higher risk of high blood pressure than non-obese people.

As described above, as the awareness that obesity itself is a fatal disease is increasing, there is a growing interest in and effort regarding weight management throughout society, and weight management methods include self-management by diet therapy and physical activities, diet food intake, lipolysis, and inhalation procedures.

However, such self-management, which involves continuously measuring one's weight using a scale and checking and recording one's weight change, is cumbersome and not easy to implement due to the busy life patterns of modern people, and systematic counseling from weight management experts may not be available. Therefore, in many situations, loss of motivation and will, and neglect of weight management, leads to failure of weight management.

Further, in the situation of diet food intake, there are innumerable types of diet foods and different medicinal plants are used as raw materials, and it is thus difficult for users to distinguish and take in foods suitable for their physical constitution. Further, when unsafe food is ingested, serious side-effects may occur. Further, drug administration and procedures are relatively expensive, which results in a cost burden.

Therefore, there is a demand for a technique which, to effectively manage an individual's weight, learns the individual's weight, information on food ingested by the individual, and exercise information performed by the individual on a present day, and predicts a change of the weight for the next day. Specifically, there is a demand for a technique which analyzes how an individual's weight changes depending on a type and an amount of food ingested by the individual.

With regard to this, a technique which manages an individual's weight with respect to obesity is disclosed in related arts 1 and 2.

Specifically, in Korean Patent Registration No. 10-1987620 (related art 1), entitled "Method and computer-readable storage medium for estimating final weight loss using initial weight and weight loss," disclosed is a technique capable of scientifically and objectively analyzing factors influencing intermediate step weight loss and final weight loss in obesity treatment, using result data of patients who have received a specific obesity treatment such as oriental medicine intake.

Specifically, according to this technique, when factors influencing the weight loss result are found, the relationship of the factors and the weight loss is scientifically and objectively analyzed, and a predicted value of the weight loss in a next step or a final step of a reliable obesity treatment is provided to patients of the obesity treatment based on the analysis result. Accordingly, the patients are able to set an appropriate weight loss goal and a treatment period so that effective obesity treatment may be performed.

However, in related art 1, only a technique allowing the patient to achieve appropriate weight loss using result data of patients who have received oriental medicine treatment is described, while there is no disclosure regarding a technique for learning an individual's weight, information on food ingested by the individual, and physical activities performed by the individual on the present day, and predicting a change in weight for the next day.

Further, in Korean Patent Registration No. 10-1740516 (related art 2), entitled "Method for weight management" disclosed is a technique which acquires the energy consumed an the individual for one day, and predicts a possible target weight using the consumed energy.

However, in related art 2, there is no disclosure regarding a technique for analyzing how an individual's weight changes depending on a type and an amount of food ingested by the individual. Moreover, there is no disclosure regarding a technique for learning and analyzing how the individual's weight changes depending on the type or the amount of food ingested by the individual for a predetermined time to predict food to be ingested and exercise to be performed in order to lose the weight.

Therefore, there is a need for techniques relating to a personalized weight loss apparatus and a weight loss method.

The above-described background technology is technical information that the inventors have held for the derivation of the present disclosure or that the inventors acquired in the process of deriving the present disclosure. Thus, the above-described background technology cannot be regarded as known technology disclosed to the general public prior to the filing of the present application.

RELATED ART DOCUMENTS

Patent Document

Related Art 1: Korean Patent Registration No. 10-1987620 (registered on Jun. 4, 2019).

Related Art 2: Korean Patent Registration No. 10-1740516 (registered on May 22, 2017).

SUMMARY OF THE INVENTION

An aspect of the present disclosure is to effectively manage an individual's weight.

Another aspect of the present disclosure is to learn a weight, ingested food information, and performed exercise information of an individual on a present day, and calculate a predicted weight of the individual based on the learned food information and exercise information. The predicted weight calculated as described above is used to generate information such as information on food to be ingested, an amount of food to be ingested, exercise to be performed, and the amount or conditions of the exercise, with respect to a target weight set by the individual.

Further, another aspect of the present disclosure is to enable accurate management of an individual's weight by accumulating the individual's weight, the individual's ingested food information, and the individual's performed exercise information, and after a predetermined times elapses, analyzing how the individual's weight changes in accordance with the ingested food and the performed exercise, and predicting food and exercise which are personalized for the individual.

In addition, according to the present disclosure, receiving a target weight from an individual, receiving weight information of the individual, ingested food information of the individual, and performed exercise information of the individual, on a present day, calculating a predicted weight of the individual for a next day by applying a prediction model to the ingested food information of the individual and the performed exercise information of the individual, the prediction model being generated in advance to predict weight variation in accordance with ingested food information and performed exercise information, receiving actual weight information of the individual on the next day,calculating a difference between the predicted weight for the next day and the actual weight of the next day, updating the prediction model to generate a personal prediction model based on the difference between the predicted weight for the next day and the actual weight of the next day over a predetermined period and generating information on food to be ingested and information on exercise to be performed for achieving the target weight received from the individual, based on the personal prediction model.

Meanwhile, according to a personalized weight management apparatus, a first data collector configured to receive weight information of an individual, ingested food information of the individual, and performed exercise information of the individual, on a present day, a first data generator configured to calculate a predicted weight of the individual for a next day by applying a prediction model to the ingested food information and the performed exercise information, the prediction model being generated in advance to predict weight variation in accordance with ingested food information and performed exercise information, a second data collector configured to receive actual weight information of the individual on the next day, a second data generator configured to calculate a difference between the predicted weight for the next day and the actual weight of the next day and a processor configured to, update the prediction model to generate a personal prediction model based on the difference between the predicted weight for the next day and the actual weight of the next day over a predetermined period, and generate information on food to be ingested and information on exercise to be performed for achieving a target weight received from the individual, based on the personal prediction model.

Aspects of the present disclosure is not limited to those mentioned above, and other aspects and advantages not mentioned above will be understood from the following description, and become more apparent from the exemplary embodiments. It is also to be understood that the aspects of the present disclosure may be realized by means and combinations thereof set forth in claims.

A personalized weight management method is disclosed. Specifically, a personalized weight management method according to an embodiment of the present disclosure may include receiving an weight information of an individual, ingested food information of the individual, and performed exercise information of the individual on a present day, and calculating a predicted weight of the individual for a next day by applying a prediction model, which is generated in advance to predict weight variation in accordance with ingested food information and performed exercise information, to the individual's ingested food information and exercise information, and upon receiving actual weight information of the next day, calculating a difference between the predicted weight for the next day and the actual weight of the next day. Thereafter, the prediction model may be updated to a personal prediction model, in accordance with the difference between the predicted weight for the next day and the actual weight of the next day collected over a predetermined period. Once the prediction model is updated to the personal prediction model, information on food to be ingested and information on exercise to be performed in order to achieve a target weight received from the individual are generated, and personalized weight management may be accomplished.

In this situation, the ingested food information may include at least one of information on a type of ingested food or information on an amount of ingested food, and the exercise information may include at least one of information on a type of the performed exercise or information on a time of the performed exercise.

Specifically, a predicted weight of an individual for the next day may be calculated by calculating calories taken in by the individual by applying average food calorie information to the type and the amount of food ingested by the individual, calculating calories burned by the individual by applying average exercise calorie information to the type of exercise and the exercise time performed by the individual, and then predicting the individual's weight for the next day based on the calories taken in and the calories burned by the individual.

When updating the prediction model to a personal prediction model, a food calorie table of the individual and an exercise calorie table of the individual may be generated in accordance with the difference between the predicted weight for the next day and the actual weight of the next day over the predetermined period.

In this situation, the food calorie table may include information on calories estimated to be taken in by the individual in accordance with the type of food and the amount of food, and the exercise calorie table may include information on calories estimated to be burned by the individual in accordance with the type of exercise and the amount of exercise.

Meanwhile, when generating the information on food to be ingested and the information on exercise to be performed, a type of exercise performed by the individual, an exercise performance time, a type of food ingested by the individual, and an amount of ingested food by the individual may be received.

In this situation, exercise which needs to be additionally performed or food which needs to be additionally ingested in order to achieve the target weight may be proposed in accordance with the personal prediction model, based on the type of performed exercise, the exercise performance time, the type of ingested food, and the amount of ingested food.

When managing the individual's weight, exercise information to be performed in order to achieve a target weight received from the individual may be generated based on average ingested calories and average burned calories for the age and gender of the individual within a predetermined period.

Meanwhile, when receiving the ingested food information and the performed exercise information of the individual, a food ingestion time and an exercise performance time of the individual may be received.

When generating information on food to be ingested and information on exercise to be performed based on the food ingestion time and the exercise performance time of the individual, a time to ingest food and a time to perform the exercise may be generated.

A personalized weight management apparatus according to another embodiment of the present disclosure may include a first data collector configured to receive weight information of an individual, ingested food information of the individual, and performed exercise information of the individual on a present day, a first data generator configured to calculate a predicted weight of the individual for a next day by applying a prediction model, which is generated in advance to predict weight variation in accordance with ingested food information and performed exercise information, to the ingested food information and the exercise information.

Further, the personalized weight management apparatus according to this embodiment of the present disclosure may further include a second data collector configured to receive actual weight information of the next day, and a second data generator configured to calculate a difference between the predicted weight for the next day and the actual weight of the next day.

The personalized weight management apparatus may further include a processor configured to update the prediction model to a personal prediction model in accordance with the difference between the predicted weight for the next day and the actual weight of the next day over a predetermined period, and generate information on food to be ingested and information on exercise to be performed in order to achieve a target weight received from the individual, using the personal prediction model.

Further, the personalized weight management apparatus may analyze how the individual's weight changes in accordance with ingested food and performed exercise over a predetermined time by accumulating the individual's weight, the individual's ingested food information, and the individual's performed exercise information, and predict food and exercise which are personalized to the individual, to more accurately manage the individual's weight.

A personalized weight management apparatus according to another embodiment of the present disclosure may include one or more processors and a memory connected to the one or more processors.

In this situation, the memory may store an instruction configured to, when executed by a processor, cause the processor to receive weight information of an individual, ingested food information of the individual, and performed exercise information of the individual on a present day, calculate a predicted weight of the individual for a next day by applying a prediction model, which is generated in advance to predict weight variation in accordance with ingested food information and performed exercise information, to the ingested food information and the exercise information, receive actual weight information of the next day, calculate a difference between the predicted weight for the next day and the actual weight of the next day, update the prediction model to a personal prediction model in accordance with the difference between the predicted weight for the next day and the actual weight of the next day over a predetermined period, and generate information on food to be ingested and information on exercise to be performed in order to achieve the target weight received from the individual using the personal prediction model.

Other aspects and features than those described above will become apparent from the following drawings, claims, and detailed description of the present disclosure.

According to the present disclosure, in order to effectively manage an individual's weight, it is possible to learn a weight, ingested food information, and performed exercise information of an individual on a present day, and calculate a predicted weight of the individual based on the learned food information and exercise information. The predicted weight calculated as described above may be used to generate information such as information on food to be ingested, an amount of food to be ingested, exercise to be performed, and the number or conditions of exercises to be performed, with respect to a target weight set by the individual.

Further, according to the present disclosure, it is possible to analyze how an individual's weight changes in accordance with ingested food and performed exercise over a predetermined time by accumulating the individual's weight, the individual's ingested food information, and the individual's performed exercise information, and predict food and exercise which are personalized to the individual, to more accurately manage the individual's weight.

The effects of the present disclosure are not limited to those mentioned above, and other effects not mentioned can be clearly understood by those skilled in the art from the following description.

BRIEF DESCRIPTION OF THE DRAWINGS

The above and other aspects, features, and advantages of the present disclosure will become apparent from the detailed description of the following aspects in conjunction with the accompanying drawings, in which.

DETAILED DESCRIPTION OF THE EMBODIMENTS

Figure 1:
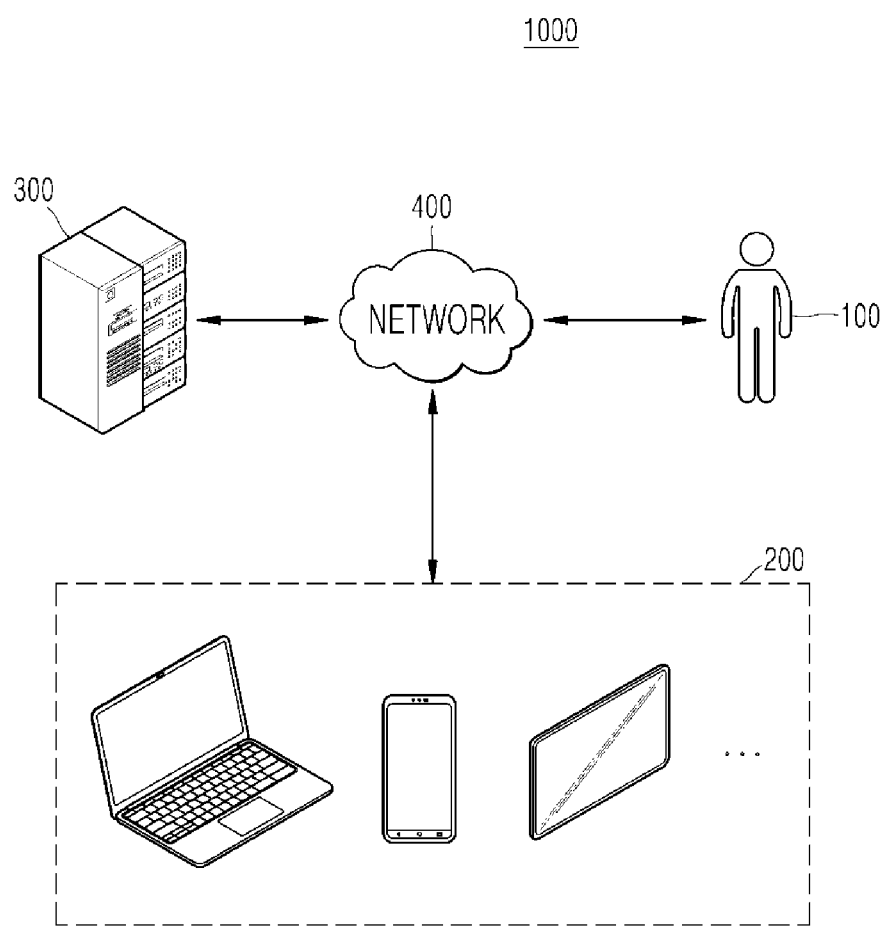
FIG. 1 is an example diagram illustrating an individual's weight management apparatus according to an embodiment of the present disclosure.

Hereinafter the embodiments disclosed in this specification will be described in detail with reference to the accompanying drawings. The present disclosure may be embodied in various different forms and is not limited to the embodiments set forth herein. Hereinafter in order to clearly describe the present disclosure, parts that are not directly related to the description are omitted. However, in implementing an apparatus or a system to which the spirit of the present disclosure is applied, it is not meant that such an omitted configuration is unnecessary. Further, like reference numerals refer to like elements throughout the specification.

In the following description, although the terms "first," "second," and the like may be used herein to describe various elements, these elements should not be limited by these terms. These terms may be only used to distinguish one element from another element. Also, in the following description, the articles "a," "an," and "the," include plural referents unless the context clearly dictates otherwise.

In the following description, it will be understood that terms such as "comprise," "include," "have," and the like are intended to specify the presence of stated feature, integer, step, operation, component, part or combination thereof, but do not preclude the presence or addition of one or more other features, integers, steps, operations, components, parts or combinations thereof.

Figure 2A:
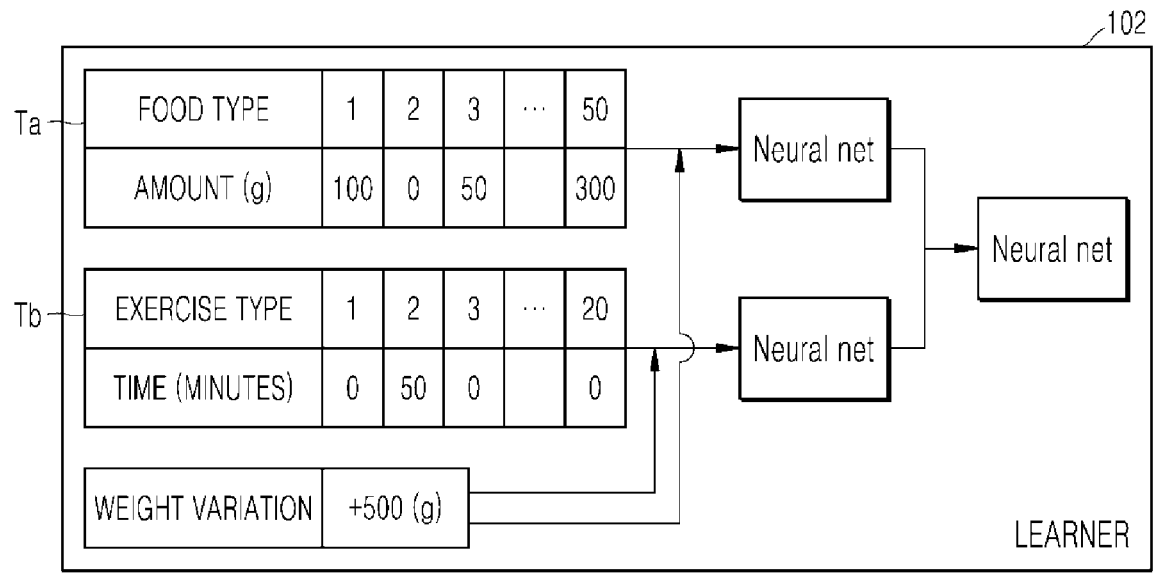
FIGS. 2A and 2B are example diagrams illustrating data collection and prediction of a predicted weight of an individual using the collected data, through the individual's weight management apparatus of FIG. 1 according to embodiments of the present disclosure.
Figure 2B:
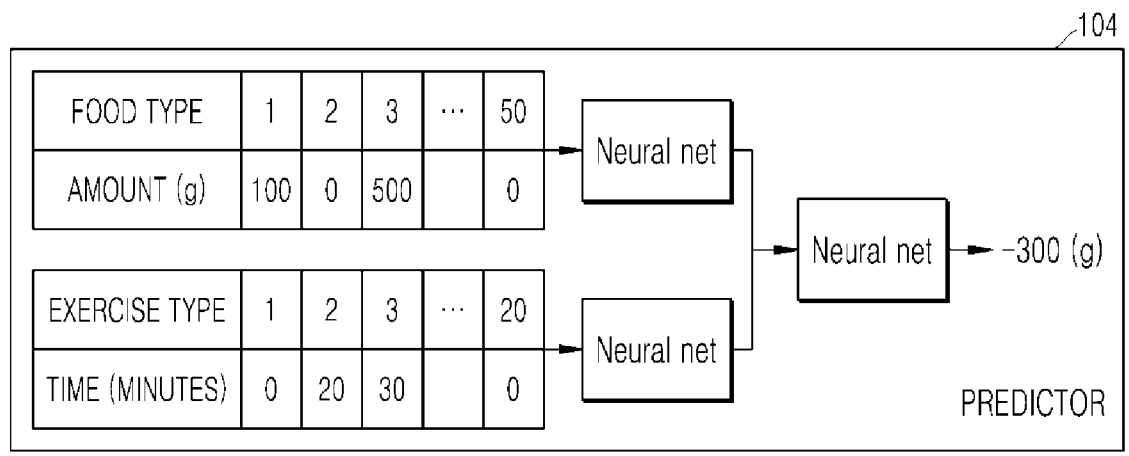
Figure 3:
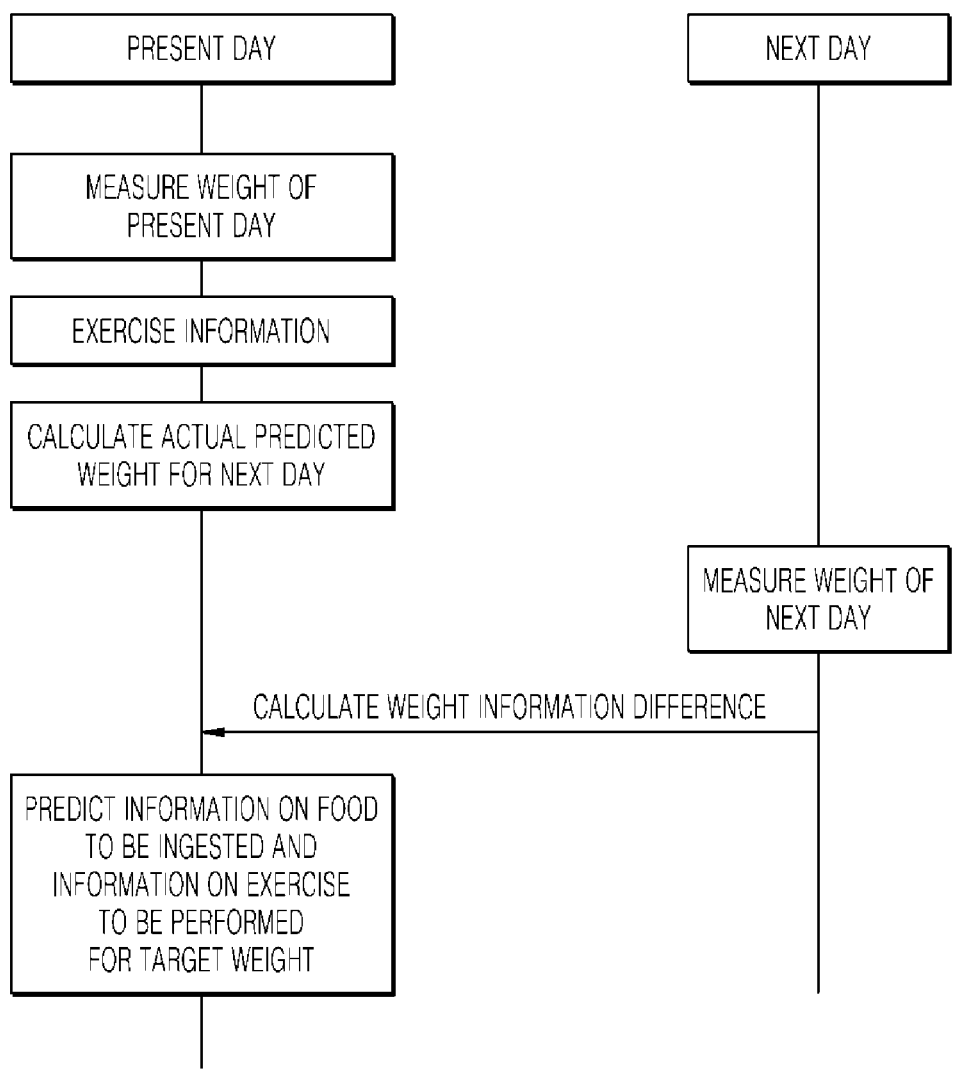
FIG. 3 is a flowchart illustrating predicted weight prediction of an individual through an individual's weight management apparatus according to an embodiment of the present disclosure.

FIG. 1 is an example diagram illustrating an individual's weight management apparatus according to an embodiment of the present disclosure. FIGS. 2A and 2B are diagrams illustrating data collection and prediction of a predicted weight of an individual using the collected data, through the individual's weight management apparatus of FIG. 1. FIG. 3 is a flowchart illustrating predicted weight prediction of an individual through an individual's weight management apparatus according to an embodiment of the present disclosure.

Referring to FIG. 1, an individual's weight management apparatus 1000 according to an embodiment of the present disclosure includes an individual 100 which manages an individual's weight, an electronic device 200 in which information of the individual 100 who uses the apparatus 1000 is stored, a central controller 300 which is connected to the electronic device 200 and controls the connected electronic device 200, and a network 400 which connects the above-mentioned components.

In the electronic device 200, information for using the weight management apparatus 1000 may be stored. As personal information, information on an individual's weight, information on a type of food and an amount of food ingested by the individual, and information on a type of exercise performed by the individual and a performance time depending on the type of exercise may be stored.

The electronic device 200 may be, for example, any one of a personal mobile communication device, a tablet PC, or a PC, and the electronic device 200 may be configured such that various electronic devices in an IoT environment communicate with each other through 5G communication.

The electronic device 200 is connected to the central controller 300 (to be described below) using wired or wireless communication, and executes a weight management service for an individual provided by the central controller 300 through the web or an application. That is, the electronic device 200 may provide, through the central controller 300 at a remote place spaced apart from the indoor space, information about the individual to drive and control the individual's weight management apparatus 1000 installed in the electronic device 200.

In this situation, the individual's weight management apparatus 1000 installed in the electronic device 200 may be implemented as an application (app).

The central controller 300 is connected to the electronic device 200 to control and monitor the operation of the electronic device 200. Further, the central controller 300 may set a weight management schedule for the individual in accordance with the personal information stored in the electronic device 200, and identify whether the individual's weight management is being performed in accordance with the set weight management schedule. Further, the central controller 300 may be configured by a single device or a plurality of devices, and when the central controller is configured by a plurality of devices, the central controller may include a hub, a central watt-hour meter advance control platform (ACP), and a management server mounted with a management program.

The network 400 may serve to connect the electronic device 200 and the central controller 300 for the purpose of central control and control by external connection.

Specifically, the network 400 may include a wired network such as a local area network (LAN), a wide area network (WAN), a metropolitan area network (MAN), or an integrated service digital network (ISDN), and a wireless network such as a wireless LAN, a CDMA, Bluetooth®, or satellite communication, but the present disclosure is not limited to these examples.

The network 400 may send and receive information by using short distance communication and/or long distance communication. The short distance communication may include Bluetooth®, radio frequency identification (RFID), infrared data association (IrDA), ultra-wideband (UWB), ZigBee, and wireless fidelity (Wi-Fi) technologies, and the long distance communication may include code division multiple access (CDMA), frequency division multiple access (FDMA), time division multiple access (TDMA), orthogonal frequency division multiple access (OFDMA), and single carrier frequency division multiple access (SC-FDMA).

The network 400 may include a connection of network elements such as a hub, a bridge, a router, a switch, and a gateway. The network 400 may include one or more connected networks, for example, a multi-network environment, including a public network such as an Internet and a private network such as a safe corporate private network. Access to the network 400 may be provided through one or more wire-based or wireless access networks. Further, the network 400 may support 5G communications and/or an Internet of things (IoT) network for exchanging and processing information between distributed components such as objects.

Further, the central controller 300 and the electronic device 200 may be connected through the network 400, such as a building automation control network (BACnet). In this situation, a gateway may be further provided.

In FIGS. 2A and 2B, an individual's weight management apparatus 1000 which collects personal data and predicts a predicted weight of an individual using the collected data is illustrated.

For example, the individual's weight management apparatus 1000 may include a learner 102 and a predictor 104. Specifically, the learner 102 may receive information on a type and an amount of food ingested by the individual over a predetermined period and information on a type of exercise and an exercise time performed by the individual over a predetermined period.

The information on the ingested food and the information on the performed exercise received as described above may be learned by the predictor 104 over a predetermined period. Artificial intelligence may be used to learn the personal information received from the individual. Although the artificial intelligence will be described in detail below, briefly, the personal information received from the individual is used as learning data, and a prediction model capable of predicting variation of the individual's weight is created and trained based on the learning data.

Based on a result predicted by the prediction model for predicting variation of the individual's weight using artificial intelligence as described above, a type and an amount of food to be ingested, a type of exercise to be performed, and an exercise performance time may be provided to the individual, and the individual may implement the actions proposed in the received information.

The learner 102 and the predictor 104 may be processors which are executable by being stored in an application installed in the electronic device 200 for managing the weight of the individual 100. Here, "processor" may, for example, refer to a data processing device embedded in hardware, which has a physically structured circuitry to perform a function represented by codes or instructions contained in a program.

Referring to FIG. 3, weight information, ingested food information, and exercise information of the individual on the present day may be received by the electronic device 200. In accordance with the received information, a predicted weight for a next day following the present day may be calculated based on a personal prediction model for predicting an individual's weight variation.

Specifically, in a state in which the weight information, the ingested food information, and the performed exercise information of the individual for the present day have been received, the individual's weight for the next day is calculated. Thereafter, in a state in which the predicted weight for the next day has been calculated, the individual's actual weight on the next day is received from the individual, and the difference between the received individual's actual weight on the next day and the individual's weight that was received on the previous day may be calculated.

The individual's weight variation may be predicted in accordance with the calculated difference of the actual weight information of the next day following the present day. The personal prediction model may be updated in accordance with the individual's predicted weight variation. For example, when an individual's weight on the next day following the present day decreases, the predicted weight may be reduced, and when the individual's weight on the next day following the present day increases, the predicted weight may be increased.

Meanwhile, the individual's weight variation information may be collected and stored over a predetermined period, and the personal prediction model may be trained in accordance with the individual's weight variation collected and stored over a predetermined period. For example, the individual's weight management apparatus 1000 may learn the predicted weight over a period designated by the individual, or learn the predicted weight over a previously received period.

As described above, when the predicted weight of the individual is learned over a predetermined period, a type and an amount of food to be ingested by the individual, a type of exercise to be performed, and an exercise performance time in accordance with the type of exercise may be predicted with respect to a target weight inputted by the individual.

As a result, information about food ingested by the individual over a predetermined period, a type and an amount of ingested food, and a type and a time of exercise performed by the individual is received by the weight management apparatus of the present disclosure. How much food and what type of food needs to be ingested, and what exercise and how much of the exercise needs to be performed, in order to effectively manage (gain or lose) the weight, may be predicted through the received information. The individual is then notified of the predicted result and may implement the actions proposed in the predicted result, and weight management can thereby be accomplished.

Figure 4:
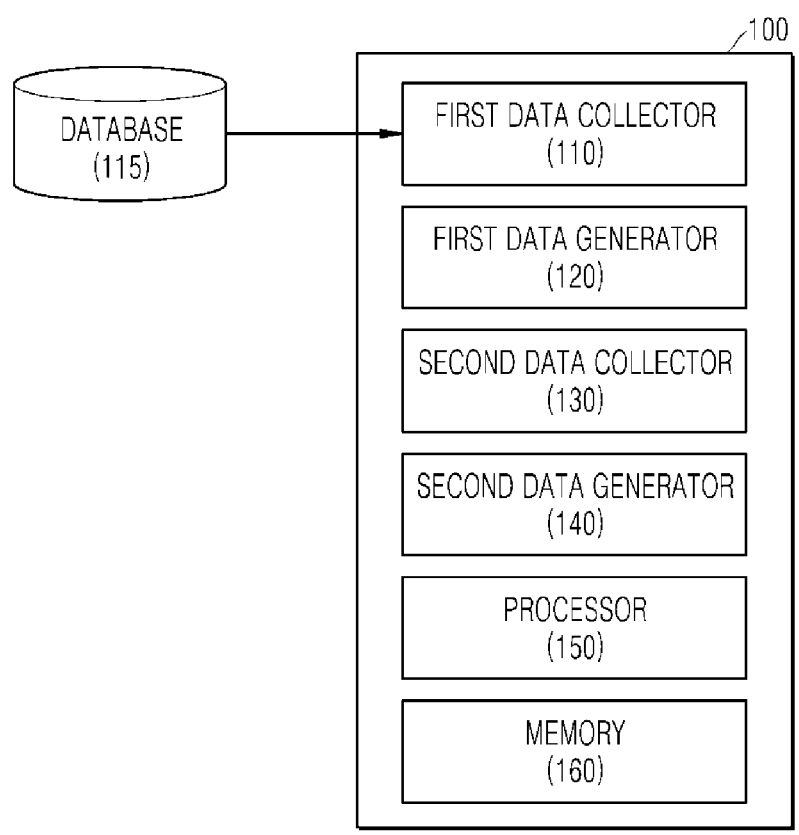
FIG. 4 is a block diagram illustrating a schematic configuration of an individual's weight management apparatus according to an embodiment of the present disclosure.
Figure 5:
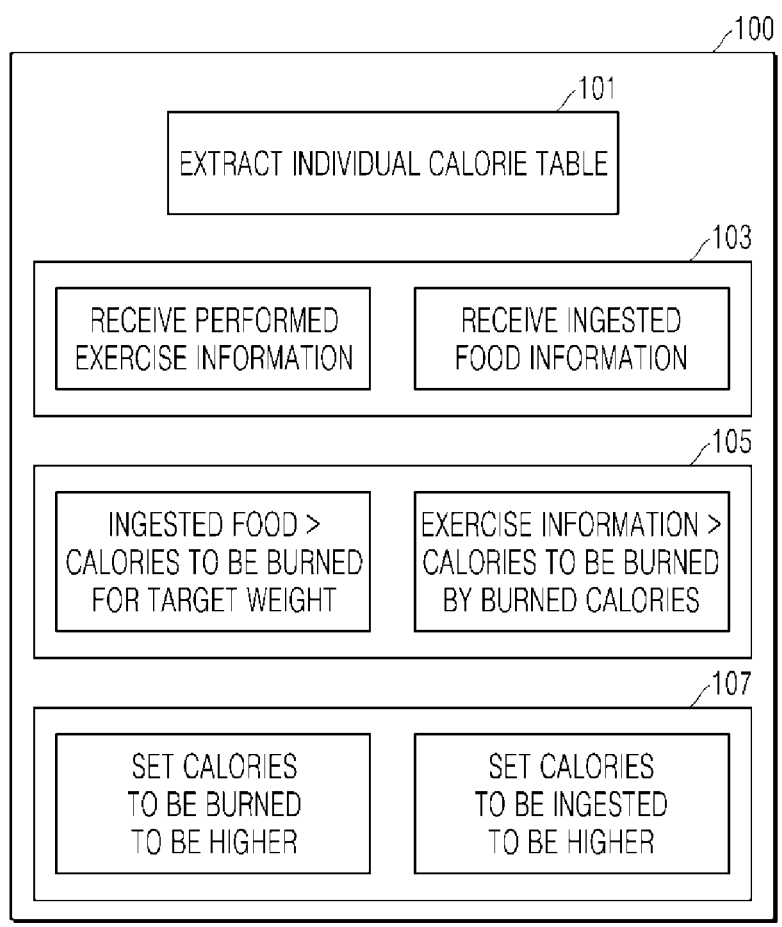
FIG. 5 is a block diagram specifically illustrating a processor of FIG. 4 according to an embodiment of the present disclosure.

FIG. 4 is a block diagram illustrating a schematic configuration of an individual's weight management apparatus according to an embodiment of the present disclosure, and FIG. 5 is a block diagram specifically illustrating a processor of FIG. 4. In the following description, descriptions of reference numerals overlapping with those of FIGS. 1 to 3 will be omitted for convenience of description.

According to an embodiment of the present disclosure, the individual's weight management apparatus 1000 may include a first data collector 110, a first data generator 120, a second data collector 130, a second data generator 140, and a processor 150.

The first data collector 110 may receive weight information of an individual on the present day, ingested food information of the individual, and exercise information of the individual. Specifically, when the first day on which the individual's weight management apparatus 1000 is executed is assumed as the present day, personal information for the present day may be acquired.

Here, the ingested food information may be information about a type and an amount of food ingested by the individual, and the exercise information may be information about a type of exercise performed by the individual and the exercise performance time.

The personal information received by the first data collector 110 may be used to calculate a predicted weight for the next day following the present day, using the first data generator 120.

Specifically, the first data generator 120 may calculate a predicted weight for the next day following the present day based on the calculated ingested food information and exercise information, based on a prediction model which is generated in advance to predict weight variation in accordance with ingested food information and performed exercise information.

That is, calories taken in through food eaten by the individual on the present day and calories burned through exercise performed by the individual on the present day are calculated, and by adding the calculated calories to or subtracting the calculated calories from the individual's weight measured on the present day, a variation of the individual's weight is calculated.

Here, in order to calculate the calories taken in through the food eaten and the calories burned through the exercise performed by the individual on the present day, a difference between the calories generally contained in the food and the calories generally burned by the performed exercise may be calculated.

Meanwhile, the processor 150 (to be described below) may apply average food calorie information to the type of food and the amount of food ingested by the individual, which are collected by the first data collector 110.

Thereafter, when the average food calorie information is applied to the individual's food information, average exercise calorie information is applied to the calories taken in by the individual and the type of exercise and exercise time performed by the individual, and the weight of the individual for the next day is predicted based on the calories burned by the individual and the calories taken in by the individual.

When the predicted weight for the next day following the present day is calculated as described above, actual weight information of the individual of the next day following the present day may be received through the second data collector 130.

After receiving the individual's actual weight information of the next day following the present day using the second data collector 130, the second data generator 140 may calculate a difference between the individual's weight information of the present day and the actual weight information of the next day.

When the difference between the individual's weight information and the actual weight information of the next day following the present day is calculated, the prediction model may be updated to a personal prediction model in accordance with the difference calculated by the processor 150. In this situation, the personal prediction model may be an artificial intelligence capable of predicting the individual's weight variation based on the personal information received from the individual.

That is, the difference between the weight information of the present day and the actual weight information of the next day following the present day changes every day. Generally, since the present day may be today and the next day may be the next day following today, the difference between the weight information of the present day and the actual weight information of the next day following the present day may change every day, and the personal prediction model may be updated in accordance with the calculated difference. Specifically, a type of food and the amount of food to be ingested by the individual, a type of exercise to be performed, and an exercise performance time may change from day to day, and the individual's weight variation may thus be predicted based on the changed food information and exercise information.

Further, the processor 150 may learn the changed predicted weight over a predetermined period. Specifically, the processor collects and learns information such as information on the type and amount of food ingested by the individual, and information on the type of performed exercise and the exercise performance time.

The processor 150 may generate an food calorie table of the individual and an exercise calorie table of the individual in accordance with the difference between the predicted weight for the next day following the present day and the actual weight of the next day, based on the learned information (101, see FIG. 5).

Here, the individual's food calorie table and the individual's exercise calorie table may a table including information on calories estimated to be taken in by the individual in accordance with the type of food and the amount of food and information on calories estimated to be burned by the individual in accordance with the type of exercise and the amount of exercise, respectively (103, see FIG. 5).

Specifically, in the table, a type and an amount of food ingested by the individual by date, the calories thereof, and the calories burned for the type and the time of the exercise performed by the individual are calculated.

The individual's food calorie table and the individual's exercise calorie table generated as described above may be used as information for generating, using the updated personal prediction model, information on food to be ingested and information on exercise to be performed for the target weight set by the individual.

That is, when the individual's calorie table is generated, information on food to be ingested and information on exercise to be performed in order to achieve a target weight received from the individual may be predicted based on the generated table. For example, calories burned as compared with the food ingested, in accordance with the type and the amount of food ingested by the individual and the exercise performed and the performance time over a predetermined period, may be calculated (105, see FIG. 5).

Based on the calculated information on calories burned as compared with the ingested food, information about exercise which needs to be additionally performed in order to lose weight or food which needs to be additionally ingested in order to gain weight may be proposed in order to achieve the target weight, in accordance with the personal prediction model.

Specifically, under the assumption that on the present day, the individual ingests more calories than he/she ingested in a previous period, when the target weight is lower than the current weight, more calories need to be burned in order to achieve the target weight. Therefore, the processor 150 may set the amount of exercise to be performed to be higher, based on information on the food which has already been ingested (107, see FIG. 5).

For example, when it is assumed that a static exercise such as yoga is usually performed, if the user has taken in a high amount of calories, the processor may set a dynamic exercise as exercise to be performed (for example, cardiovascular exercise such as running). Alternatively, when the individual intends to perform the same exercise as the exercise that he or she performed in the previous period, the exercise time is set to be long, to provide guidance to the individual to achieve the target weight.

Alternatively, in the individual's calorie table, the calories burned due to a completed exercise amount with respect to the exercise information of the individual on the present day may be higher than the calories to be burned. In this situation, the information on food to be ingested in order to achieve the target weight may be updated (107, see FIG. 5).

Specifically, when the burned calories are higher than the calories to be burned, the burned calories are supplemented by ingesting the food, and accordingly, when the target weight received from the individual is higher than the weight received on the present day, it is possible to gain the weight.

In this situation, the predetermined period may refer to a period of a day or longer, stored in advance in the individual's weight management apparatus 1000, and for example, may be 30 days. Hereinafter, in the exemplary embodiment of the present disclosure, the predetermined period may refer to 30 days as a reference, but the present disclosure is not limited to this reference period.

Meanwhile, the personalized weight management apparatus 1000 may collect and store the individual's predicted weight within the predetermined period. In this situation, based on average calories ingested per food and average calories burned per exercise according to the age and gender of the individual, the information on food to be ingested and the information on exercise to be performed in order to achieve the target weight received from the individual may be generated.

For example, information on average calories that should be ingested and average calories that should be burned according to age and gender may be pre-stored in the memory 160 (to be described below) of the individual's weight management apparatus 1000 and an external server, and according to the stored average ingested calories and average burned calories, the calories to be ingested by the individual and the calories to be burned by the individual may be predicted.

Meanwhile, data about the predicted weight learned in the processor 150 may be stored in an information database 115. Further, in the information database 115, information about types of food, calories of the types of food, types of exercise, and calories burned in accordance with performance time for each type of exercise may also be stored.

Further, the first data collector 110, the first data generator 120, the second data collector 130, and the second data generator 140 described in the embodiment of the present disclosure may be processors which are executable by being stored in an application installed in the electronic device 200 for managing the weight of the individual 100. The configuration may include any type of devices which are capable of processing data, for example, MCU. Here, the "processor" may, for example, refer to a data processing device embedded in hardware, which has a physically structured circuitry to perform a function represented by codes or instructions contained in a program.

As examples of the data processing device embedded in hardware, a microprocessor, a central processor (CPU), a processor core, a multiprocessor, an application-specific integrated circuit (ASIC), and a field programmable gate array (FPGA) may be included, but the scope of the present disclosure is not limited thereto.

Meanwhile, in the embodiment of the present disclosure, as an example, the individual's predicted weight is predicted based on the ingested food information and the performed exercise information received from the individual, and information on food to be ingested and information on exercise to be performed in order to achieve the received target weight are predicted based on the individual's predicted weight. However, the information on food to be ingested in order to achieve the received target weight may also be predicted based on information on foods and ingredients stored in a refrigerator used by the individual.

For example, the individual may photograph the inside of the refrigerator used by the individual using a personal mobile communication device. An amount of calories which needs to be burned when any one food among the foods stored in the refrigerator is ingested by the individual is immediately calculated through the photographed image, and the information on exercise to be performed may be predicted on this basis.

Further, the photographed food ingredient information stored in the refrigerator is stored, and foods which can be ingested by the individual are predicted based on the stored food material information, or foods which can be ingested are notified to the individual. Accordingly, the individual is enabled to effectively manage his or her weight.

Further, in order to predict the food to be ingested by the individual and the exercise to be performed by the individual, the processor 150 may receive a food ingestion time and an exercise performance time of the individual.

Specifically, the individual's food ingestion time and the individual's exercise performance time for a period of one day may be received. When the food ingestion time and the exercise performance time over a predetermined period are received, a time to ingest food and a time to perform exercise may be predicted for the individual. The predicted food ingestion time and exercise performance time are notified to the individual. Accordingly, weight management suitable for the individual's schedule may be accomplished.

Meanwhile, in order to effectively manage the individual's weight, the exercise information and the ingested food information received from the individual, and the information on average calories that should be ingested and average calories that should be burned according to age and gender, may be stored in the memory 160.

Specifically, the memory 160 may be connected to one or more processors 150, and when the one or more processors 150 are executed, an instruction causing the one or more processors 150 to predict information on food to be ingested and information on exercise to be performed in order to effectively manage the weight of the individual, based on the weight information, the ingested food information, and the exercise information of the individual for the present day, which are received over a predetermined period, may be stored.

That is, the individual's predicted weight is learned based on the individual's ingested food information and performed exercise information over a predetermined period, and information on food to be ingested and information on exercise to be performed in order to achieve the target weight received from the individual based on the learned individual's predicted weight are provided to the individual.

The learning may be performed by a device capable of managing the individual's weight, but may also be performed by a separate external device. Only the information for predicting information on food to be ingested and information on exercise to be performed for the target weight received from the individual which are deduced as the learning result may be stored in the central controller 300 connected to a system capable of managing the individual's weight.

Further, various types of information to predict information on food to be ingested and information on exercise to be performed in order to achieve the target weight received from the individual are stored in the memory 160, and the memory 160 may include a volatile or a non-volatile recording medium. The recording medium is for storing data capable of being read by the controller 150 and may include, for example, a hard disk drive (HDD), a solid state drive (SSD), a silicon disk drive (SDD), a ROM, a RAM, a CD-ROM, a magnetic tape, a floppy disk, and an optical data storage device. In this embodiment, the information stored in the memory unit 160 will be described in a context appropriate for each situation.

In the embodiment of the present disclosure, an example will be described in which information for predicting information on food to be ingested and information on exercise to be performed in order to achieve the target weight received from the individual, which are stored in the memory 160, is received from an external server. The server may be a database server which provides big data to apply various artificial intelligence algorithms and data for speech recognition.

Meanwhile, the processor 150, which is capable of predicting the information on food to be ingested and the information on exercise to be performed in order to achieve the target weight received from the individual, may include any kind of device capable of processing data. Here, the "processor" may, for example, refer to a data processing device embedded in hardware, which has a physically structured circuitry to perform a function represented by codes or instructions contained in a program. As examples of the data processing device embedded in hardware, a microprocessor, a central processor (CPU), a processor core, a multiprocessor, an application-specific integrated circuit (ASIC), and a field programmable gate array (FPGA) may be included, but the scope of the present disclosure is not limited thereto.

Figure 6:
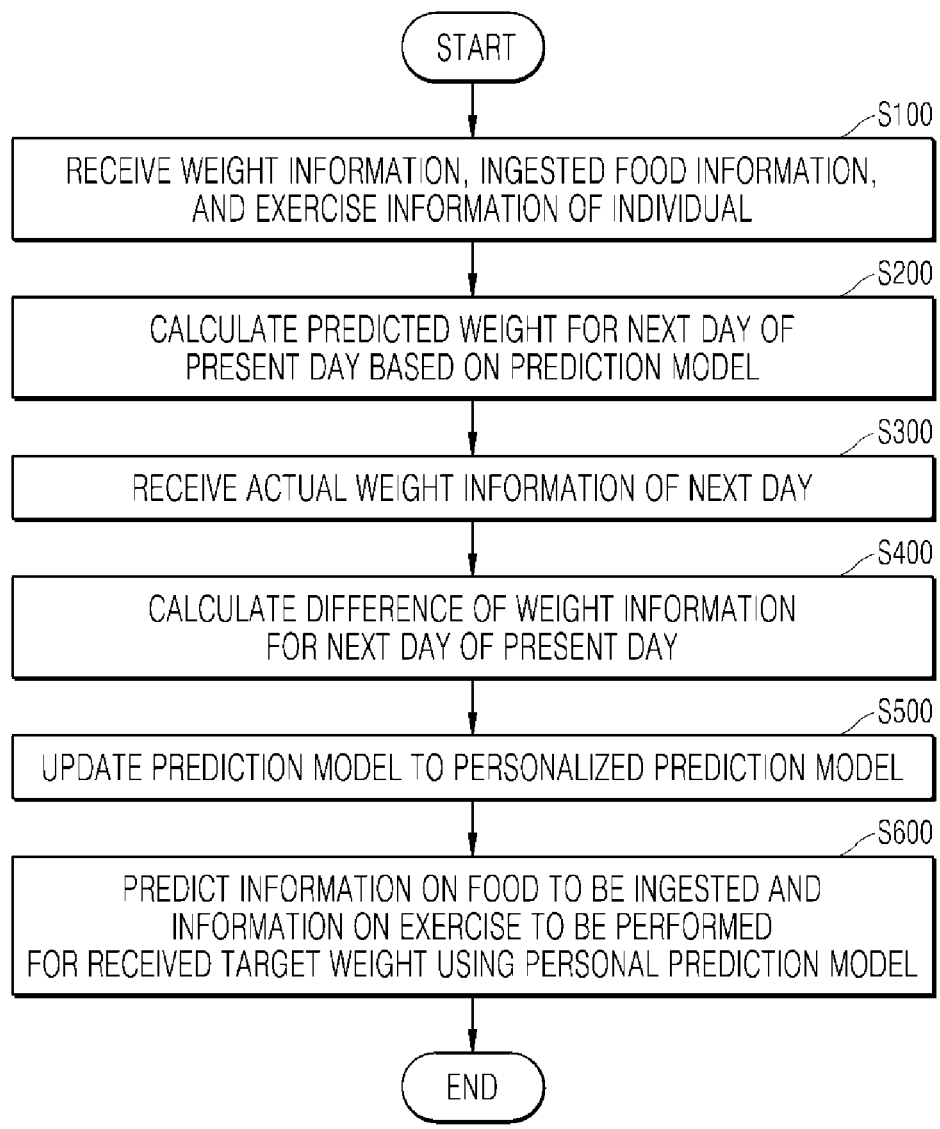
FIG. 6 is a flowchart schematically illustrating a personalized weight management method according to an embodiment of the present disclosure.
Figure 7:
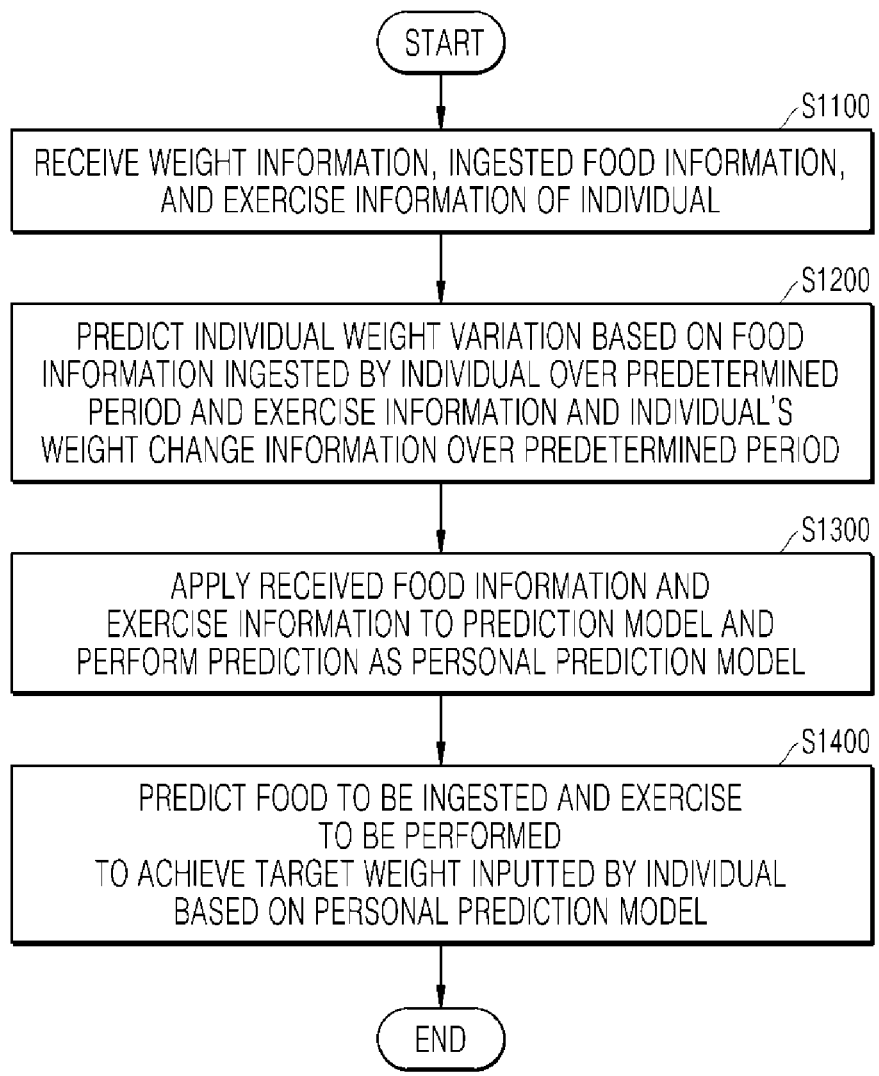
FIG. 7 is a flowchart schematically illustrating a personalized weight management method according to another embodiment of the present disclosure.

FIG. 6 is a flowchart schematically illustrating a personalized weight management method according to an embodiment of the present disclosure. FIG. 7 is a flowchart schematically illustrating a personalized weight management method according to another embodiment of the present disclosure. In the following description, description of the parts that are the same as those in FIG. 1 to FIG. 6 will be omitted.

First, referring to FIG. 6, an individual's weight management apparatus 1000 installed in an electronic device 200 receives weight information of the individual, ingested food information of the individual, and exercise information of the individual for a present day (S100). Specifically, when the first day on which the individual's weight management apparatus 1000 is executed is assumed the present day, personal information for the present day may be acquired.

Here, the ingested food information may be information about a type and an amount of food ingested by the individual, and the exercise information may be information about a type of exercise performed by the individual and the exercise performance time.

After the weight information, the ingested food information, and the exercise information of the individual for the present day is received, in accordance with the received ingested food information and exercise information, a predicted weight of the individual for the next day following the present day is calculated based on a prediction model which is generated in advance to predict weight variation in accordance with ingested food information and exercise information (S200).

Specifically, the predicted weight for the next day following the present day may be calculated based on the ingested food information and the exercise information calculated based on the prediction model which is generated in advance to expect a weight variation in accordance with ingested food information and performed exercise information.

Thereafter, when average food calorie information is applied to the individual's food information, the average exercise calorie information is applied to the calories taken in by the individual and the type of exercise and exercise time performed by the individual, and a weight of the individual for the next day is predicted based on the calories burned by the individual and the calories taken in by the individual.

Specifically, actual weight information of the individual on the next day following the present day is received, and the weight of the individual for the next day is predicted by calculating a difference between the weight information of the present day and the actual weight information of the next day (S300 and S400).

When the predicted weight for the next day following the present day is calculated as described above, actual weight information of the next day following the present day is received, and a difference between the received actual weight of the individual of the next day and the previously received weight of the individual of the present day may be calculated.

When the difference between the individual's weight information of the present day and the actual weight information of the next day following the present day is calculated, the prediction model may be updated to a personal prediction model in accordance with the difference calculated by the processor 150 (S500).

The personal prediction model may be a learning model which predicts an individual's weight variation in accordance with personal information. Specifically, the learning model may be updated to predict weight variation for the next day in accordance with the individual's ingested food information and performed exercise information.

Specifically, the difference between the weight information of the present day and the actual weight information of the next day following the present day changes every day. Generally, since the present day may be today and the next day may be the next day following today, the difference between the weight information of the present day and the actual weight information of the next day following the present day may change every day, and the personal prediction model may be updated in accordance with the calculated difference.

Thereafter, the individual's predicted weight may be learned over a predetermined period. Specifically, this means that information such as the type and the amount of food ingested by the individual, and the type of exercise and exercise time performed by the individual, is learned.

The processor 150 may predict information on food to be ingested and information on exercise to be performed for a target weight received from the individual, in accordance with the difference between the predicted weight for the next day following the present day and the actual weight of the next day (S600).

According to the details of the process of predicting information on food to be ingested and information on exercise to be performed in order to achieve a target weight received from the individual, calories burned as compared with the ingested food, in accordance with the type and amount of food ingested by the individual and the exercise performed by the individual and the performance time over a predetermined period, needs to be calculated. Information about exercise which needs to be additionally performed in order to lose weight or food which needs to be additionally ingested in order to gain weight may be proposed in order to achieve the target weight, in accordance with the personal prediction model based on the calculated information on calories burned as compared with the ingested food.

Specifically, under the assumption that on the present day, the individual ingests more calories than he/she ingested in a previous period, when the target weight is lower than the current weight, more calories need to be burned in order to achieve the target weight. Therefore, an amount of exercise to be performed may be set to be higher, based on information on the food which has already been ingested.

Alternatively, in a calorie table of the individual, the calories burned due to a completed exercise amount with respect to the exercise information of the individual on the present day may be higher than the calories to be burned. In this situation, information on food to be ingested in order to achieve the target weight may be updated.

Specifically, when the burned calories are higher than the calories to be burned, the burned calories are supplemented by ingesting the food, and accordingly, when the target weight received from the individual is higher than the weight received on the present day, it is possible to gain the weight.

Meanwhile, after the predicted weight of the individual for the next day has been calculated (S200) and the actual weight information of the next day has been received (S300), during the process (S400 and S500) of calculating the difference between the individual's weight information for the present day and the actual weight information of the next day following the present day to predict the weight for the next day, and updating the prediction model to a personal prediction model in accordance with the difference between the predicted weight for the next day and the actual weight of the next day over a predetermined period, the individual's predicted weight may be collected and stored within a predetermined period.

In this situation, based on average calories ingested per food and average calories burned per exercise according to the age and gender of the individual, the information on food to be ingested and the information on exercise to be performed in order to achieve the target weight received from the individual may be generated.

For example, information on average ingested calories and average burned calories according to each age and gender may be pre-stored in the memory 160 of the individual's weight management apparatus 1000 and an external server, and calories to be ingested by the individual and calories to be burned by the individual may be predicted according to the stored average ingested calories and average burned calories.

Further, in order to predict the food to be ingested by the individual and the exercise to be performed by the individual, the processor 150 may receive a food ingestion time and the exercise performance time of the individual.

Specifically, the individual's food ingestion time and the individual's exercise performance time for a period of one day may be received. When the food ingestion time and the exercise performance time over a predetermined period are received, a time to ingest food and a time to perform exercise may be predicted. The predicted food ingestion time and exercise performance time are notified to the individual, and accordingly, weight management suitable for the individual's schedule may be accomplished.

Alternatively, when a time that the individual ingests food and a time that the individual exercises for one day are received, the information on exercise to be performed and the information on food to be ingested in order to achieve the target weight received from the individual may be predicted.

For example, when the personalized weight management apparatus 1000 receives the information on food ingested by the individual for one day, the information on exercise to be performed may be predicted based on the received food information. Alternatively, when the personalized weight management apparatus 1000 receives the exercise information performed by the individual for one day, information on calories burned is calculated through the performed exercise information in order to predict information on food to be ingested. Further, the ingested food information and the performed exercise information may be received in real time. In this situation, when it is determined that the amount of performed exercise as compared with the ingested food is small considering the target weight inputted by the individual, based on the received food and exercise information, it may be determined that the calories burned is low. In this situation, an exercise time to be performed is set to be long, or an exercise having a higher exercising amount is suggested to be performed in order to achieve the target weight inputted by the individual.

Meanwhile, referring to FIG. 7, an individual's weight management apparatus 1000 installed in an electronic device 200 receives weight information of an individual, ingested food information of the individual, and exercise information of the individual for the present day (S1100).

Next, the received food information and exercise information are applied to the prediction model to predict a varied weight of the individual (S1200).

Here, the information on food ingested by the individual may be information on the type and amount of food ingested by the individual, and the exercise information may be information on the type of exercise performed by the individual and the exercise performance time.

Thereafter, the prediction model may be updated to a personal prediction model based on the ingested food information of the individual and the performed exercise information of the individual over a predetermined period, and weight variation information of the individual over the predetermined period (S1300).

Specifically, calories for a type and an amount of food ingested by the individual for one day and calories burned by the individual for one day may vary every day. Further, the weight of the individual may vary in accordance with the calories for the type and the amount of the food ingested by the individual and the calories burned by the individual for one day. Therefore, information on a weight change of the individual according to the ingested food information and the performed exercise information over a predetermined period is updated, and the prediction model may thereby be updated to a personal prediction model capable of predicting the weight variation of the individual.

The information on food to be ingested and the information on exercise to be performed in order to achieve a target weight which is inputted by the individual may be predicted based on the updated prediction model.

As a result, information on food ingested by the individual over a predetermined period, a type and an amount of the ingested food, and a type and a time of exercise performed by the individual is received. How much food and what type of food needs to be ingested, and what exercise and how much of the exercise needs to be performed, in order to effectively manage (gain or lose) the weight, may be predicted through the received information.

Figure 8:
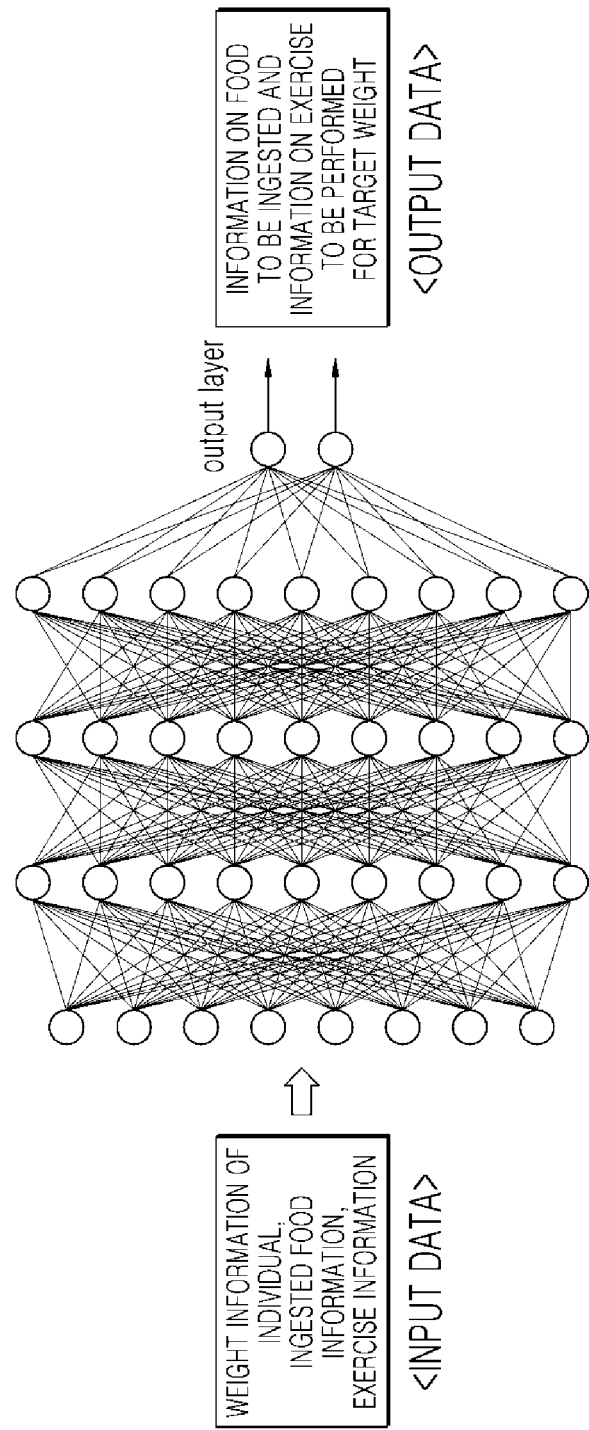
FIG. 8 is a view illustrating a deep neural network model for an individual's weight management according to an embodiment of the present disclosure.

FIG. 8 is a view illustrating a deep neural network model for an individual's weight management according to an embodiment of the present disclosure.

In order to manage the individual's weight, a deep neural network model which learns the individual's ingested food information and the individual's performed exercise information in advance using an artificial intelligence machine learning is used.

Artificial intelligence (AI) is an area of computer engineering science and information technology that studies methods to make computers mimic intelligent human behaviors such as reasoning, learning, self-improving, and the like.

In addition, artificial intelligence does not exist on its own, but is rather directly or indirectly related to a number of other fields in computer science. In recent years, there have been numerous attempts to introduce an element of the artificial intelligence into various fields of information technology to solve problems in the respective fields.

Machine learning is an area of artificial intelligence that includes the field of study that gives computers the capability to learn without being explicitly programmed.

Specifically, machine learning may be a technology for researching and constructing a system for learning, predicting, and improving its own performance based on empirical data and an algorithm for the same. Machine learning algorithms, rather than only executing rigidly set static program commands, may be used to take an approach that builds models for deriving predictions and decisions from inputted data.

Numerous machine learning algorithms have been developed for data classification in machine learning. Representative examples of such machine learning algorithms for data classification include a decision tree, a Bayesian network, a support vector machine (SVM), an artificial neural network (ANN), and so forth.

Decision tree refers to an analysis method that uses a tree-like graph or model of decision rules to perform classification and prediction.

Bayesian network may include a model that represents the probabilistic relationship (conditional independence) among a set of variables. Bayesian network may be appropriate for data mining via unsupervised learning.

SVM may include a supervised learning model for pattern detection and data analysis, heavily used in classification and regression analysis.

ANN is a data processing system modelled after the mechanism of biological neurons and interneuron connections, in which a number of neurons, referred to as nodes or processing elements, are interconnected in layers.

ANNs are models used in machine learning and may include statistical learning algorithms conceived from biological neural networks (particularly of the brain in the central nervous system of an animal) in machine learning and cognitive science.

ANNs may refer generally to models that have artificial neurons (nodes) forming a network through synaptic interconnections, and acquires problem-solving capability as the strengths of synaptic interconnections are adjusted throughout training.

The terms 'artificial neural network' and 'neural network' may be used interchangeably herein.

An ANN may include a number of layers, each including a number of neurons. Furthermore, the ANN may include synapses that connect the neurons to one another.

An ANN may be defined by the following three factors: (1) a connection pattern between neurons on different layers; (2) a learning process that updates synaptic weights; and (3) an activation function generating an output value from a weighted sum of inputs received from a lower layer.

ANNs include, but are not limited to, network models such as a deep neural network (DNN), a recurrent neural network (RNN), a bidirectional recurrent deep neural network (BRDNN), a multilayer perception (MLP), and a convolutional neural network (CNN).

An ANN may be classified as a single-layer neural network or a multi-layer neural network, based on the number of layers therein.

In general, a single-layer neural network may include an input layer and an output layer.

In general, a multi-layer neural network may include an input layer, one or more hidden layers, and an output layer.

The input layer receives data from an external source, and the number of neurons in the input layer is identical to the number of input variables. The hidden layer is located between the input layer and the output layer, and receives signals from the input layer, extracts features, and feeds the extracted features to the output layer. The output layer receives a signal from the hidden layer and outputs an output value based on the received signal. Input signals between the neurons are summed together after being multiplied by corresponding connection strengths (synaptic weights), and if this sum exceeds a threshold value of a corresponding neuron, the neuron can be activated and output an output value obtained through an activation function.

A deep neural network with a plurality of hidden layers between the input layer and the output layer may be the most representative type of artificial neural network which enables deep learning, which is one machine learning technique.

An ANN can be trained using training data. Here, the training may refer to the process of determining parameters of the artificial neural network by using the training data, to perform tasks such as classification, regression analysis, and clustering of inputted data. Such parameters of the artificial neural network may include synaptic weights and biases applied to neurons.

An artificial neural network trained using training data can classify or cluster inputted data according to a pattern within the inputted data.

Throughout the present specification, an artificial neural network trained using training data may be referred to as a trained model.

Hereinbelow, learning paradigms of an artificial neural network will be described in detail.

Learning paradigms, in which an artificial neural network operates, may be classified into supervised learning, unsupervised learning, semi-supervised learning, and reinforcement learning.

Supervised learning is a machine learning method that derives a single function from the training data.

Among the functions that may be thus derived, a function that outputs a continuous range of values may be referred to as a regressor, and a function that predicts and outputs the class of an input vector may be referred to as a classifier.

In supervised learning, an artificial neural network can be trained with training data that has been given a label.

Here, the label may refer to a target answer (or a result value) to be guessed by the artificial neural network when the training data is inputted to the artificial neural network.

Throughout the present specification, the target answer (or a result value) to be guessed by the artificial neural network when the training data is inputted may be referred to as a label or labeling data.

Throughout the present specification, assigning one or more labels to training data in order to train an artificial neural network may be referred to as labeling the training data with labeling data.

Training data and labels corresponding to the training data together may form a single training set, and as such, they may be inputted to an artificial neural network as a training set.

The training data may exhibit a number of features, and the training data being labeled with the labels may be interpreted as the features exhibited by the training data being labeled with the labels. In this situation, the training data may represent a feature of an input object as a vector.

Using training data and labeling data together, the artificial neural network may derive a correlation function between the training data and the labeling data. Then, through evaluation of the function derived from the artificial neural network, a parameter of the artificial neural network may be determined (optimized).

Unsupervised learning is a machine learning method that learns from training data that has not been given a label.

More specifically, unsupervised learning may be a training scheme that trains an artificial neural network to discover a pattern within given training data and perform classification by using the discovered pattern, rather than by using a correlation between given training data and labels corresponding to the given training data.

Examples of unsupervised learning include, but are not limited to, clustering and independent component analysis.

Examples of artificial neural networks using unsupervised learning include, but are not limited to, a generative adversarial network (GAN) and an autoencoder (AE).

GAN is a machine learning method in which two different artificial intelligences, a generator and a discriminator, improve performance through competing with each other.

The generator may be a model generating new data that generates new data based on true data.

The discriminator may be a model recognizing patterns in data that determines whether inputted data is from the true data or from the new data generated by the generator.

Furthermore, the generator may receive and learn from data that has failed to fool the discriminator, while the discriminator may receive and learn from data that has succeeded in fooling the discriminator. Accordingly, the generator may evolve to fool the discriminator as effectively as possible, while the discriminator evolves to distinguish, as effectively as possible, between the true data and the data generated by the generator.

An auto-encoder (AE) is a neural network which aims to reconstruct its input as output.

More specifically, AE may include an input layer, at least one hidden layer, and an output layer.

Since the number of nodes in the hidden layer is smaller than the number of nodes in the input layer, the dimensionality of data is reduced, thus leading to data compression or encoding.

Furthermore, the data outputted from the hidden layer may be inputted to the output layer. Given that the number of nodes in the output layer is greater than the number of nodes in the hidden layer, the dimensionality of the data increases, thus leading to data decompression or decoding.

Furthermore, in the AE, the inputted data is represented as hidden layer data as interneuron connection strengths are adjusted through training. The fact that when representing information, the hidden layer is able to reconstruct the inputted data as output by using fewer neurons than the input layer may indicate that the hidden layer has discovered a hidden pattern in the inputted data and is using the discovered hidden pattern to represent the information.

Semi-supervised learning is machine learning method that makes use of both labeled training data and unlabeled training data.

One semi-supervised learning technique involves reasoning the label of unlabeled training data, and then using this reasoned label for learning. This technique may be used advantageously when the cost associated with the labeling process is high.

Reinforcement learning may be based on a theory that given the condition under which a reinforcement learning agent can determine what action to choose at each time instance, the agent can find an optimal path to a solution solely based on experience without reference to data.

Reinforcement learning may be performed mainly through a Markov decision process.

Markov decision process consists of four stages: first, an agent is given a condition containing information required for performing a next action; second, how the agent behaves in the condition is defined; third, which actions the agent should choose to get rewards and which actions to choose to get penalties are defined; and fourth, the agent iterates until future reward is maximized, thereby deriving an optimal policy.

An artificial neural network is characterized by features of its model, the features including an activation function, a loss function or cost function, a learning algorithm, an optimization algorithm, and so forth. Also, the hyperparameters are set before learning, and model parameters can be set through learning to specify the architecture of the artificial neural network.

For instance, the structure of an artificial neural network may be determined by a number of factors, including the number of hidden layers, the number of hidden nodes included in each hidden layer, input feature vectors, target feature vectors, and so forth.

Hyperparameters may include various parameters which need to be initially set for learning, much like the initial values of model parameters. Also, the model parameters may include various parameters sought to be determined through learning.

For instance, the hyperparameters may include initial values of weights and biases between nodes, mini-batch size, iteration number, learning rate, and so forth. Furthermore, the model parameters may include a weight between nodes, a bias between nodes, and so forth.

Loss function may be used as an index (reference) in determining an optimal model parameter during the learning process of an artificial neural network. Learning in the artificial neural network involves a process of adjusting model parameters to reduce the loss function, and the purpose of learning may be to determine the model parameters that minimize the loss function.

Loss functions typically use means squared error (MSE) or cross entropy error (CEE), but the present disclosure is not limited thereto.

Cross-entropy error may be used when a true label is one-hot encoded. One-hot encoding may include an encoding method in which among given neurons, only those corresponding to a target answer are given 1 as a true label value, while those neurons that do not correspond to the target answer are given 0 as a true label value.

In machine learning or deep learning, learning optimization algorithms may be deployed to minimize a cost function, and examples of such learning optimization algorithms include gradient descent (GD), stochastic gradient descent (SGD), momentum, Nesterov accelerate gradient (NAG), Adagrad, AdaDelta, RMSProp, Adam, and Nadam.

GD includes a method that adjusts model parameters in a direction that decreases the output of a cost function by using a current slope of the cost function.

The direction in which the model parameters are to be adjusted may be referred to as a step direction, and a size by which the model parameters are to be adjusted may be referred to as a step size.

Here, the step size may mean a learning rate.

GD obtains a slope of the cost function through use of partial differential equations, using each of model parameters, and updates the model parameters by adjusting the model parameters by a learning rate in the direction of the slope.

SGD may include a method that separates the training dataset into mini batches, and by performing gradient descent for each of these mini batches, increases the frequency of gradient descent.

Adagrad, AdaDelta and RMSProp may include methods that increase optimization accuracy in SGD by adjusting the step size, and may also include methods that increase optimization accuracy in SGD by adjusting the momentum and step direction. Adam may include a method that combines momentum and RMSProp and increases optimization accuracy in SGD by adjusting the step size and step direction. Nadam may include a method that combines NAG and RMSProp and increases optimization accuracy by adjusting the step size and step direction.

Learning rate and accuracy of an artificial neural network rely not only on the structure and learning optimization algorithms of the artificial neural network but also on the hyperparameters thereof. Therefore, in order to obtain a good learning model, it is important to choose a proper structure and learning algorithms for the artificial neural network, but also to choose proper hyperparameters.

In general, the artificial neural network is first trained by experimentally setting hyperparameters to various values, and based on the results of training, the hyperparameters can be set to optimal values that provide a stable learning rate and accuracy.

In order to generate a deep neural network model used an embodiment of the present disclosure, there various methods may be used. In the situation of supervised learning, as a preliminary operation, the following training process may be performed.

The individual's weight management apparatus 1000 may receive information on food ingested by the individual over a predetermined period, a type and an amount of ingested food, and a type and a time of exercise performed by the individual. A learning dataset may be configured to predict, through the received information, how much food and what type of food needs to be ingested, and what exercise and how much of the exercise needs to be performed, in order to effectively manage (gain or lose) the weight.

When the deep neural network model is trained with the training data, the trained learning model reflects features of the individual, and provides information on food to be ingested and information on exercise to be performed that is suitable for managing the weight of the particular individual.

The individual consistently provides feedback regarding the determination result of the deep neural network model, thereby refining the learning model.

The example embodiments described above may be implemented through computer programs executable through various components on a computer, and such computer programs may be recorded on computer-readable media. Examples of the computer-readable medium may include, but are not limited to: magnetic media such as hard disks, floppy disks, and magnetic tapes; optical media such as CD-ROM disks and DVD-ROM disks; magneto-optical media such as floptical disks; and hardware devices that are specially configured to store and execute program commands, such as ROM, RAM, and flash memory devices.

The computer programs may be those specially designed and constructed for the purposes of the present disclosure or they may be of the kind well known and available to those skilled in the computer software arts. Examples of computer programs may include both machine codes, such as produced by a compiler, and higher-level codes that may be executed by the computer using an interpreter.

As used in the present disclosure (especially in the appended claims), the singular forms "a," "an," and "the" include both singular and plural references, unless the context clearly states otherwise. Also, it should be understood that any numerical range recited herein is intended to include all sub-ranges subsumed therein (unless expressly indicated otherwise) and therefore, the disclosed numeral ranges include every individual value between the minimum and maximum values of the numeral ranges.

Also, the order of individual steps in process claims of the present disclosure does not imply that the steps must be performed in this order; rather, the steps may be performed in any suitable order, unless expressly indicated otherwise. In other words, the present disclosure is not necessarily limited to the order in which the individual steps are recited. Also, the steps included in the methods according to the present disclosure may be performed through the processor or modules for performing the functions of the step. All examples described herein or the terms indicative thereof ("for example," etc.) used herein are merely to describe the present disclosure in greater detail. Therefore, it should be understood that the scope of the present disclosure is not limited to the example embodiments described above or by the use of such terms unless limited by the appended claims. Also, it should be apparent to those skilled in the art that various modifications, combinations, and alternations can be made depending on design conditions and factors within the scope of the appended claims or equivalents thereof.

The present disclosure is thus not limited to the example embodiments described above, and rather intended to include the following appended claims, and all modifications, equivalents, and alternatives falling within the spirit and scope of the following claims.

What is claimed is:

1. A method of controlling a device to perform personalized weight management, the method comprising:
   collecting, by a processor in the device, weight variation information from an individual over a predetermined previous training period;
   receiving, by the processor, a target weight from the individual after the predetermined previous training period has ended;
   receiving, by the processor, weight information of the individual, ingested food information of the individual, and performed exercise information of the individual, on a present day;
   calculating, by the processor, a predicted weight of the individual for a next day by applying a prediction model to the ingested food information of the individual and the performed exercise information of the individual, the prediction model being generated in advance to predict weight variation in accordance with ingested food information and performed exercise information;
   receiving, by the processor, actual weight information of the individual on the next day;
   calculating, by the processor, a difference between the predicted weight for the next day and the actual weight of the next day;
   training, by the processor, the prediction model by performing an artificial neural network training operation based on the difference between the predicted weight for the next day and the actual weight of the next day over a predetermined period and the weight variation information corresponding to the predetermined previous training period to generate an updated personal prediction model; and
   generating, by the processor, information on food to be ingested and information on exercise to be performed for achieving the target weight received from the individual, based on the updated personal prediction model, wherein the prediction model is an artificial neural network, and the artificial neural network training operation includes updating parameters of the prediction model and adjusting a number of nodes within layers of the prediction model.

2. The method according to claim 1, wherein:
the ingested food information comprises at least one of information on a type of ingested food or information on an amount of ingested food; and
the performed exercise information comprises at least one of information on a type of performed exercise or information on an amount of exercise performance time.

3. The method according to claim 2, wherein the calculating the predicted weight of the individual for the next day comprises:
calculating calories taken in by the individual based on average food calorie information for the type and the amount of food ingested by the individual;
calculating calories burned by the individual based on average exercise calorie information for the type of exercise and the amount of exercise performance time performed by the individual; and
predicting the weight of the individual for the next day based on the calories taken in by the individual and the calories burned by the individual.

4. The method according to claim 3, wherein the updating the prediction model comprises generating a food calorie table of the individual and an exercise calorie table of the individual based on the difference between the predicted weight for the next day and the actual weight of the next day over the predetermined period,
wherein the food calorie table comprises information on calories estimated to be taken in by the individual based on the type of food and the amount of food, and
wherein the exercise calorie table comprises information on calories estimated to be burned by the individual based on the type of exercise and the amount of exercise.

5. The method according to claim 3, wherein the generating the information on food to be ingested and the information on exercise to be performed comprises:
receiving a type of exercise performed by the individual and an amount of exercise performance time for type of exercise performed;
receiving a type of food ingested by the individual and an amount of the type of food ingested by the individual; and
recommending additional exercise to be additionally performed or additional food to be additionally ingested for achieving the target weight in accordance with the updated personal prediction model, based on the type of performed exercise, the amount of exercise performance time for the type of exercise performed, the type of ingested food, and the amount of type of ingested food.

6. The method according to claim 1, further comprising:
generating information on food to be ingested and information on exercise to be performed for achieving the target weight received from the individual, based on average calories ingested per food item and average calories burned per exercise according to an age and gender of the individual within the predetermined period.

7. The method according to claim 1, wherein the receiving the ingested food information of the individual and the performed exercise information of the individual comprises receiving a food ingestion time of the individual and an amount of exercise performance time of the individual.

8. The method according to claim 7, wherein the generating of the information on food to be ingested and the information on exercise to be performed comprises generating a time of day to ingest the food and a time of day to perform the exercise.

9. A non-transitory computer readable recording medium storing a computer program configured to execute the method according to claim 1.

10. An apparatus for personalized weight management, comprising:
a storage configured to store weight management information for an individual; and
a processor configured to:
collect weight variation information from an individual over a predetermined previous training period,
receive weight information of the individual, ingested food information of the individual, and performed exercise information of the individual, on a present day after the predetermined previous training period has ended,
receive a predicted weight of the individual for a next day calculated by applying a prediction model to the ingested food information of the individual and the performed exercise information of the individual, the prediction model being generated in advance to predict weight variation in accordance with ingested food information and performed exercise information,
receive actual weight information of the individual on the next day,
receive a difference between the predicted weight for the next day and the actual weight of the next day,
train the prediction model by performing an artificial neural network training operation based on the difference between the predicted weight for the next day and the actual weight of the next day over a predetermined period and the weight variation information corresponding to the predetermined previous training period to generate an updated personal prediction model, and
generate information on food to be ingested and information on exercise to be performed for achieving a target weight received from the individual, based on the updated personal prediction model,
wherein the artificial neural network training operation includes updating parameters of the prediction model and adjusting a number of nodes within layers of the prediction model, and
wherein the updated personal prediction model is a multi-layer neural network including an input layer, an output layer and one or more hidden layers between the input layer and the output layer.

11. The apparatus according to claim 10, wherein the ingested food information comprises at least one of information on a type of ingested food or information on an amount of ingested food, and the performed exercise information comprises at least one of information on a type of performed exercise and information on an amount of exercise performance time.

12. The apparatus according to claim 11, wherein the processor is further configured to:
calculate calories taken in by the individual based on average food calorie information for the type and the amount of food ingested by the individual;

calculate calories burned by the individual based on average exercise calorie information for the type of exercise and the exercise time performed by the individual; and predict the weight of the individual for the next day based on the calories taken in by the individual and the calories burned by the individual.

13. The apparatus according to claim 12, wherein the processor is further configured to:

generate a food calorie table of the individual and an exercise calorie table of the individual based on the difference between the predicted weight for the next day and the actual weight of the next day over the predetermined period, wherein the food calorie table comprises information on calories estimated to be taken in by the individual based on the type of food and the amount of food, and wherein the exercise calorie table comprises information on calories estimated to be burned by the individual based on the type of exercise and the amount of exercise.

14. The apparatus according to claim 12, wherein the processor is further configured to:

receive a type of exercise performed by the individual and an amount of exercise performance time for the type of exercise performed by the individual, receive a type of food ingested by the individual and an amount of the type of food ingested by the individual, and recommend information on additional food to be ingested and information on additional exercise to be performed.

15. The apparatus according to claim 10, wherein the processor is further configured to:

generate information on food to be ingested and information on exercise to be performed for achieving the target weight received from the individual, based on average calories ingested per food item and average calories burned per exercise based on an age and gender of the individual within the predetermined period.

16. The apparatus according to claim 10, wherein the processor is further configured to:

receive a food ingestion time of the individual and an amount of exercise performance time of the individual.

17. The apparatus according to claim 16, wherein the processor is further configured to:

generate a time of day to ingest the food and a time of day to perform the exercise.

18. An apparatus for personalized weight management, comprising:

one or more processors; and a memory connected to the one or more processors, wherein the one or more processors are configured to:

collect weight variation information from an individual over a predetermined previous training period, receive weight information of an individual, ingested food information of the individual, and performed exercise information of the individual on a present day after the predetermined previous training period has ended, calculate a predicted weight of the individual for a next day by applying a prediction model, to the ingested food information and the performed exercise information, the prediction model being generated in advance to predict weight variation in accordance with ingested food information and performed exercise information, receive actual weight information of the individual on the next day, calculate a difference between the predicted weight for the next day and the actual weight of the next day, train the prediction model by performing an artificial neural network training operation based on the difference between the predicted weight for the next day and the actual weight of the next day over a predetermined period and the weight variation information corresponding to the predetermined previous training period to generate an updated personal prediction model, and generate information on food to be ingested and information on exercise to be performed for achieving a target weight received from the individual, based on the updated personal prediction model, wherein the artificial neural network training operation includes updating parameters of the prediction model and adjusting a number of nodes within layers of the prediction model, and wherein the updated personal prediction model is a multilayer neural network including an input layer, an output layer and one or more hidden layers between the input layer and the output layer.

19. The apparatus of claim 18, wherein the ingested food information comprises at least one of information on a type of ingested food or information on an amount of ingested food, and the performed exercise information comprises at least one of information on a type of performed exercise and information on an amount of exercise performance time.

20. The apparatus of claim 18, wherein the one or more processors are further configured to:

generate information on food to be ingested and information on exercise to be performed for achieving the target weight received from the individual, based on average calories ingested per food item and average calories burned per exercise based on an age and gender of the individual within the predetermined period.

* * * * *